(12) United States Patent
Ales et al.

(10) Patent No.: US 7,667,608 B2
(45) Date of Patent: Feb. 23, 2010

(54) WETNESS DEVICE LOCK AND KEY AND DEVICE ID

(75) Inventors: Thomas M. Ales, Neenah, WI (US); Darold D. Tippey, Brunswick, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 262 days.

(21) Appl. No.: 11/799,046

(22) Filed: Apr. 30, 2007

(65) Prior Publication Data

US 2008/0269702 A1 Oct. 30, 2008

(51) Int. Cl.
*G08B 23/00* (2006.01)
*A61M 1/00* (2006.01)
*A61F 13/15* (2006.01)
*A61F 13/20* (2006.01)

(52) U.S. Cl. ............... 340/573.5; 604/318; 604/361
(58) Field of Classification Search ............ 340/573.5; 604/358, 361, 318; 600/584
See application file for complete search history.

(56) References Cited

U.S. PATENT DOCUMENTS

| | | | |
|---|---|---|---|
| 4,106,001 A * | 8/1978 | Mahoney .................. 340/604 |
| 4,704,116 A | 11/1987 | Enloe |
| 4,940,464 A | 7/1990 | Van Gompel et al. |
| 5,342,583 A * | 8/1994 | Son ........................ 422/107 |
| 5,760,694 A * | 6/1998 | Nissim et al. ............ 340/604 |
| 5,766,389 A | 6/1998 | Brandon et al. |
| 5,838,240 A * | 11/1998 | Johnson .................. 340/604 |
| 5,903,222 A * | 5/1999 | Kawarizadeh et al. ..... 340/604 |
| 6,097,297 A * | 8/2000 | Fard ........................ 340/604 |
| 6,573,837 B2 * | 6/2003 | Bluteau .................... 340/604 |
| 6,645,190 B1 | 11/2003 | Olson et al. |
| 7,145,053 B1 * | 12/2006 | Emenike et al. .......... 604/361 |
| 7,250,547 B1 * | 7/2007 | Hofmeister et al. ....... 604/361 |
| 7,394,391 B2 | 7/2008 | Long et al. |
| 2002/0070868 A1 | 6/2002 | Jeutter et al. |
| 2004/0106202 A1 * | 6/2004 | Zainiev et al. ............ 436/39 |
| 2005/0137542 A1 * | 6/2005 | Underhill et al. ......... 604/361 |
| 2007/0024457 A1 | 2/2007 | Long et al. |
| 2007/0083174 A1 | 4/2007 | Ales |
| 2007/0252710 A1 | 11/2007 | Long et al. |

FOREIGN PATENT DOCUMENTS

WO WO 0037009 A2 6/2000

OTHER PUBLICATIONS

International Search Report for International Application No. PCT/IB2008/050805, dated Sep. 23, 2008.

* cited by examiner

*Primary Examiner*—Jennifer Mehmood
(74) *Attorney, Agent, or Firm*—Dority & Manning, P.A.

(57) ABSTRACT

The present subject matter relates to absorbent articles and signaling devices for use therewith. An absorbent article may be provided with selected electrical components used as wetness or other type sensors and may also incorporate one or more electrical components, characteristics of which may be determined by a coupled signaling device. An attached signaling device may automatically determine a product identification based on characteristics of the electrical components detected and adjust operating characteristics or parameters for the sensing device. Determinations could be made based on gender, age and approximate weight of the user of the absorbent device. In addition automatic checks can be made to determine mutual operability of the signaling device with an associated absorbent article or visa-versa.

20 Claims, 3 Drawing Sheets

WETNESS DEVICE LOCK AND KEY AND DEVICE ID

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent articles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants identify a wet diaper condition early on. The devices produce either a visual or an audible signal.

In some embodiments, for instance, inexpensive conductive threads, foils, or paper have been placed in the absorbent articles in the machine direction. The conductive materials serve as conductive leads for a signaling device and form an open circuit in the article that can be closed when a body fluid, such as urine, closes the circuit. In these embodiments, although the absorbent articles may be disposable, the signaling devices are not. Thus, the signaling devices are intended to be removed from the article and reattached to a subsequent article.

Problems, however, have been encountered in accurately identifying and interpreting signals derived from insult to the conductive layers due to the variety of absorbent articles to which signaling devices may be coupled. Further problems have been identified relating to the possible use of unknown signaling devices that may not function properly if coupled to specially designed absorbent articles.

SUMMARY OF THE INVENTION

In general, the present disclosure is directed to improved wetness sensing and signaling arrangements for use with a variety of absorbent articles. Signaling devices corresponding to various configurations may be attached by appropriate mechanisms to disposable absorbent articles. The signaling device, for instance, may be configured to indicate to a user that a body fluid is present in the absorbent article. For example, in one embodiment, the absorbent article comprises a diaper and the signaling device is configured to indicate the presence of urine or of a bowel movement. In other embodiments, however, the signaling device may be configured to indicate the presence of yeast or metabolites depending upon the particular type of absorbent article that is used in conjunction with the signaling device.

In one embodiment, the absorbent article of the present invention includes conductive leads that extend, for instance, in the longitudinal direction of the article. The conductive leads can be made from relatively inexpensive materials and therefore can be disposable with the absorbent article. The signaling device, however, may be configured to be reused multiple times and with multiple different specific absorbent articles. Thus, the present disclosure is directed to a simple and efficient manner of automatically identifying the absorbent article type to which the signaling device is attached.

In one particular embodiment, the absorbent article comprises a chassis including an outer cover having an interior surface and an exterior surface. An absorbent structure is positioned adjacent to the interior surface of the outer cover. If desired, a liquid permeable body-side liner may also be incorporated into the chassis on the opposite side of the absorbent structure. The chassis may include a crotch region positioned in between a front region and a back region. The front region and the back region may define a waist region therebetween.

First and second conductive elements may be contained in the chassis. The conductive elements may be made from, for instance, a conductive thread, a conductive foil, or conductive paper and may extend from the waist region to at least the crotch region of the chassis without intersecting. These conductive elements can form a simple open circuit (for wetness sensing for example) and may also be provided with serial or parallel connected electrical components that may be employed in combination with the signaling device to determine a number absorbent article related parameters.

One or more conductive pad members may be electrically connected to the first conductive element and a further conductive pad member may be electrically connected to the second conductive element. Such conductive pad members may take various forms, some of which are more fully described in co-pending U.S. patent application Ser. No. 11/405,263, entitled "Connection Mechanisms In Absorbent Articles For Body Fluid Signaling Devices" filed Apr. 17, 2006, assigned to the assignee of the present subject matter, and incorporated herein for all purposes. The exact configuration of the conductive pad members is not critical to the present disclosure, it being sufficient to note that the pad members are each configured to electrically connect to a signaling device. For instance, when a known signaling device is properly attached to the conductive pad members and a body fluid is present between the first and second conductive elements, the open circuit between the conductive elements is closed for activating the signaling device.

The signaling device itself may comprise a single unit that attaches to the absorbent article. Alternatively, the signaling device may include a transmitter that attaches to the absorbent article and a receiver that is configured to receive a wireless signal from the transmitter. The receiver, for instance, may indicate to a user that a body fluid has insulted the absorbent article remote from the article itself. In either configuration, the signaling device is configured to produce user perceptible signals.

The signaling device may be configured to indicate the presence of a body fluid in various ways. For example, the signaling device may emit a visible alarm and/or an audible alarm. In still another embodiment, the signaling device may be configured to vibrate when a body fluid is sensed.

Further the signaling device may include sensing circuitry designed to determine selected characteristics of the absorbent article to which it is attached. Such characteristics include, but are not limited to, the size of the absorbent article, i.e., whether the article is sized for an infant, an adult or intermediate sizes, the approximate weight of the individual who may wear the absorbent article, the sex of the wearer, whether the article and signaling device are properly configured for joint operation, and whether the signaling device is properly connected to the absorbent article. Commonly owned U.S. patent application Ser. No. 11/412,351, filed Apr. 26, 2006, incorporated herein for all purposes, describes a feedback source to the consumer to assure that they have connected the device correctly to the product.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to absorbent articles adapted to be attached to a signaling device that may be configured to indicate the presence of a body fluid in the absorbent article or other changes in the condition of the product or wearer. The absorbent article may be, for instance, a diaper, a training pant, an incontinence product, a feminine hygiene product, a medical garment, a bandage, and the like. Absorbent articles made according to the present disclosure may include a sensing circuit that detects when a conductive fluid, such as a body fluid, is sensed between a pair of conductive leads. Generally, the absorbent articles containing the sensing circuit are disposable meaning that they are designed to be discarded after a limited use rather than being laundered or otherwise restored for reuse.

The sensing circuit contained within the absorbent articles of the present disclosure is configured to be attached to a signaling device. The signaling device can provide power to the sensing circuit while also including some type of audible and/or visible signal that indicates to the user the presence of a body fluid. Although the absorbent article itself is disposable, the signaling device may be reusable from article to article. In this regard, the present disclosure is particularly directed to determining selected characteristics of different types of absorbent articles to which the signaling device may be attached. For example, the sensing circuit contained in the absorbent article may include identifiable electrical components whose electrical characteristics may be selected based on, but not limited to, the type of absorbent article, the size of the article and hence the approximate weight of the wearer, and the sex of the wearer. Further, the sensing circuit contained in the absorbent article may include one or more additional electrical components and/or conductive lead configuration designed to determine whether the sensing device being attached is appropriate for the absorbent article or, alternatively, whether the absorbent article and sensing device are mutually compatible.

As more fully described in the aforementioned co-pending, commonly assigned application, the conductive pad members may comprise a conductive loop-type material that is adapted to be connected to a conductive hook-type material disposed on the signaling device or vice versus. Alternatively, the conductive pad members may comprise a conductive film or other similar material and may be engageable by a prong or a conductive tab for connection to the signaling device. A wide variety of connection mechanisms are envisioned including those disclosed in the aforementioned incorporated patent application. It should, however, be strictly borne in mind that the particulars of such connection mechanisms are not a limitation of the present subject matter. Further, it should be realized by those of ordinary skill in the art that any type of connection mechanism may be used with the presently disclosed subject matter so long as the connection mechanism is capable of supplying sensing signals to the signaling device. It should further be appreciated that while the aforementioned incorporated patent application as well as the exemplary disclosure contained herein are more specifically directed to direct electrical connection between the conductive leads and the signaling device, such is also not a limitation of the present disclosure as other connection types including, for example, but not limited thereto, capacitive or inductive coupling, may be used.

As described above, the open circuit in combination with the signaling device may be configured to indicate the presence of a body fluid contained within the absorbent article. The particular targeted body fluid may vary depending upon the particular type of absorbent article and the desired application. For instance, in one embodiment, the absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine, such as a polysaccharide.

Figure 1:
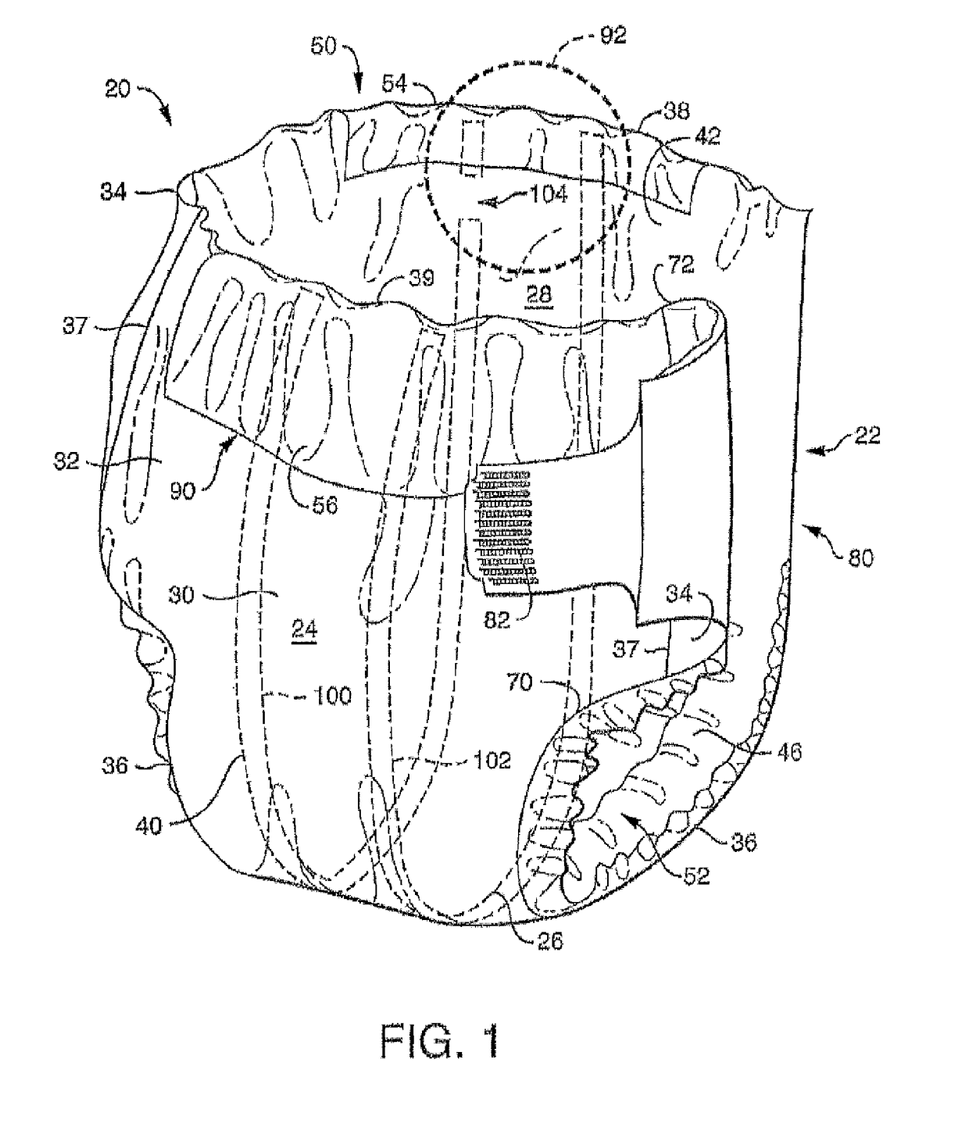
FIG. 1 is a rear perspective view of one embodiment of an absorbent article made in accordance with the present invention.

Referring to FIG. 1, for exemplary purposes, an absorbent article 20 that may be made in accordance with the present invention is shown. The absorbent article 20 may or may not be disposable. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

A more thorough exposition of the characteristics of the exemplary illustrated absorbent article 20 may be had by reference to the previously mentioned incorporated application. The following is provided as a general explanation to establish for those of ordinary skill in the art the relationship of the presently disclosed subject matter to such an exemplary absorbent article.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. The chassis 32 includes an outer cover 40 and a bodyside liner 42 that may be joined to the outer cover 40 in a superimposed relation therewith by adhesives, ultrasonic bonds, thermal bonds or other conventional techniques. The elasticized containment flaps 46 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

As shown in FIG. 1, the absorbent article 20 further includes a pair of opposing elastic side panels 34 that are attached to the back region of the chassis 32. Side panels 34 may be stretched around the waist and/or hips of a wearer in order to secure the garment in place. Elastic side panels 34 are attached to the chassis along a pair of opposing longitudinal edges 37. Side panels 34 may be attached or bonded to the chassis 32 using any suitable bonding technique. For instance, the side panels 34 may be joined to the chassis by adhesives, ultrasonic bonds, thermal bonds, or other conventional techniques.

With the absorbent article 20 in the fastened position as partially illustrated in FIG. 1, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

The fastening system 80 may include laterally opposite first fastening components 82 adapted for refastenable engagement to corresponding second fastening components (not visible) located on the front region 22 of the chassis 32.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to improved wetness sensing and signaling arrangements for use with a variety of absorbent articles 20. In this regard, as shown in FIG. 1, the absorbent article 20 includes a first conductive element 100 spaced from a second conductive element 102. In this embodiment, the conductive elements extend from the front region 22 of the absorbent article to the back region 24 without intersecting. The conductive elements 100 and 102 can comprise any suitable conductive material, such as a conductive thread or a conductive foil. The first conductive element 100 does not intersect the second conductive element 102 in order to form an open circuit that may be closed, for instance, when a conductive fluid is positioned in between the conductive elements.

Figure 2:
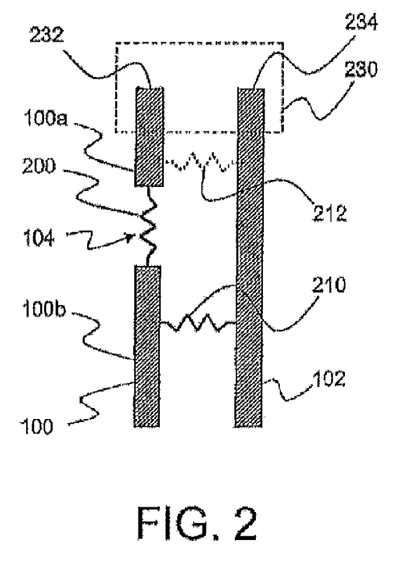
FIG. 2 is schematic representation of an exemplary configuration of conductive leads and associated electrical components as may be incorporated into the absorbent article shown in FIG. 1.
Figure 3:
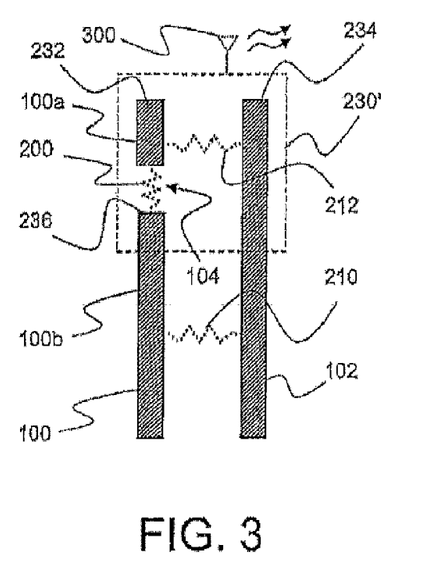
FIG. 3 is schematic representation of a second exemplary configuration of conductive leads and associated electrical components as may be incorporated into the absorbent article shown in FIG. 1.

In the embodiment shown in FIG. 1, the conductive element 102 extends the entire length of the absorbent article 20 while conductive element 100 extends the entire length of the absorbent article but may include a discontinuity 104 as may be seen within the dashed circle 92 of FIG. 1 and as illustrated in FIGS. 2-3. As will be more fully described later, various electrical elements may be connected across discontinuity 104 and may also be coupled between conductive elements 100 and 102 for specialized signaling purposes in accordance with the present subject matter.

Conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outer cover 40. In fact, in one embodiment, the conductive elements 100 and 102 may be attached or laminated to the inside surface of the outer cover 40 that faces the absorbent structure 44. Alternatively, however, the conductive elements 100 and 102 may be positioned on the absorbent structure 44 or positioned on the liner 42.

In order for the conductive elements 100 and 102 to be easily connected to a signaling device, various conductive pad members (exemplarily illustrated at 104, 106 in FIG. 5) may be provided as more thoroughly described in the previously noted incorporated application. It is sufficient to note for purposes of explaining the present subject matter that electrical connections may be easily made to various portions or segments of conductive elements 100 and 102 to practice the technology presently disclosed and that the specific methodology or apparatus used to effect such electrical connections is not a limitation to the present subject matter.

Figure 5:
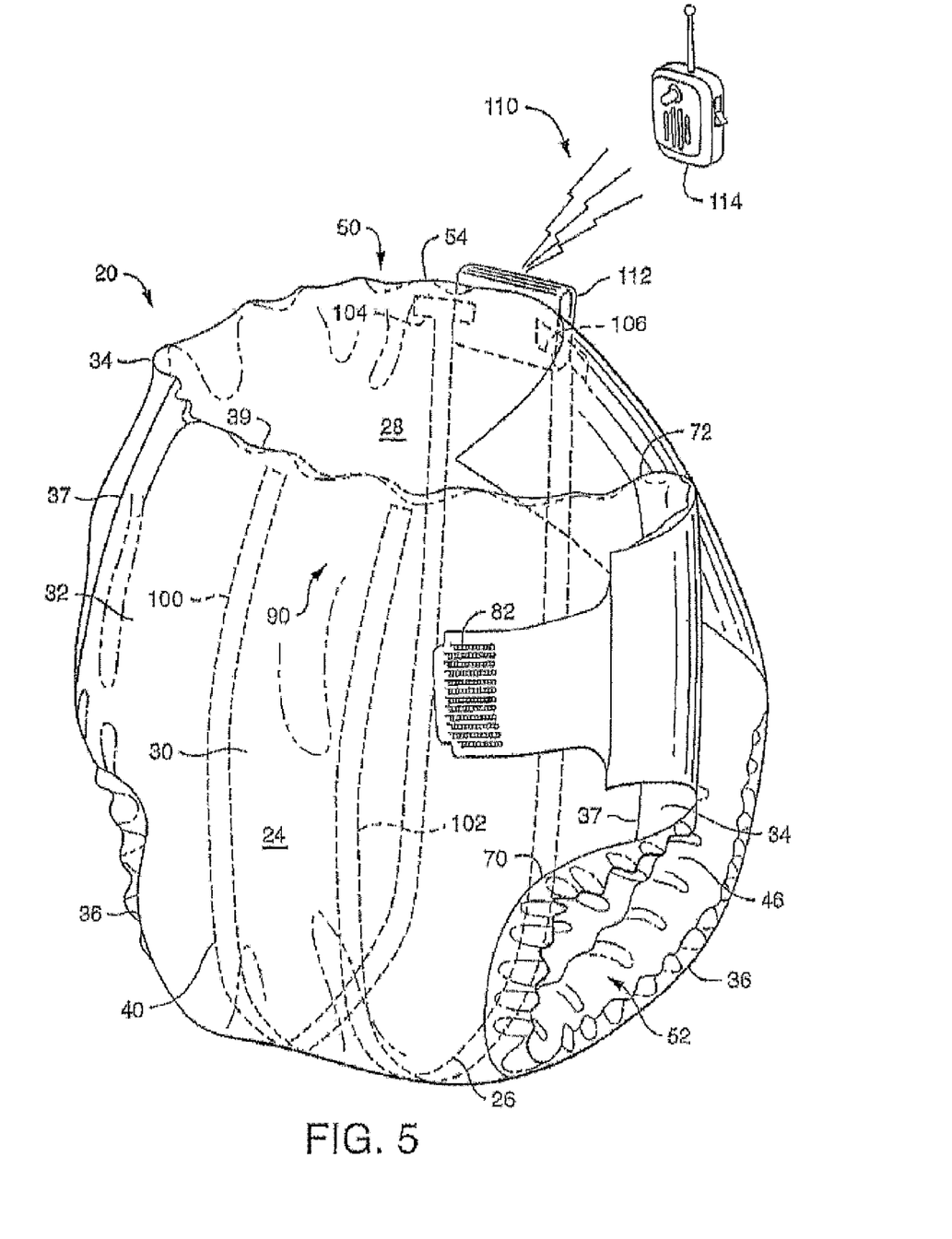
FIG. 5 is a perspective view of the embodiment shown in FIG. 1 further illustrating an exemplary embodiment of a signaling device.

Referring to FIG. 5, for exemplary purposes, a signaling device 110 is shown attached to representative conductive pad members 104 and 106. As shown, in this embodiment, the signaling device 110 generally includes a transmitter 112 and a receiver 114. The transmitter 112 includes a pair of opposing terminals that are electrically connected to the corresponding conductive pad members. When a body fluid is present in the absorbent article 20, the open circuit formed by the conductive elements 100 and 102 is closed which, in turn, activates the signaling device 110. In particular, in this embodiment, the transmitter 112 sends a wireless signal to the receiver 114 which then indicates to a user that a body fluid is present in the absorbent article.

The signaling device 110 can emit an audible and/or a visual signal in order to indicate to the user that the circuit has been closed. The audible signal, for instance, may be as simple as one or more beeps to perhaps emitting a musical tune. In certain exemplary embodiments of the present subject matter, such a musical tune may be gender and age appropriate. Similarly, if the signaling device 110 issues a visible signal, the visible signal may comprise a few lights or an interactive display. In still another embodiment, the receiver 114 of the signaling device 110 may be configured to vibrate when the circuit within the absorbent article is closed. In some embodiments of the present subject matter selected combination or all of the signaling techniques including, but not limited to vibration, visible signals, and audio signals may be employed.

As described above, the signaling device 110 can be configured to indicate the presence of any suitable conductive fluid within the absorbent article 20. The fluid may comprise, but is not limited to, urine, a metabolite, and other fluids or combinations of such fluids.

In the embodiment shown in FIG. 5, signaling device 110 includes a separately housed transmitter 112 in combination with a separately housed receiver 114. It should also be understood, however, that the signaling device may comprise a single unit that remains attached to the absorbent article 20. For example, the signaling device may be mounted on the absorbent article and issue a visible signal and/or an audible signal from the article itself. Different attachment mechanisms between the conductive pad members and the signaling device have been extensively described in the previously mentioned incorporated application and will not be further described herein.

With reference now to FIG. 2, there is illustrated a first exemplary embodiment of the present subject matter as may be incorporated into an absorbent article 20 as previously discussed. As may be seen in FIG. 2, conductive elements 100 and 102 correspond to those previously described with reference to FIGS. 1 and 5 and may be considered to correspond to a pair of substantially parallel conductors. Conductive element 100 differs from conductive element 102 in that there may be provided a gap 104 proximate one end of conductive element 100 such that conductive element 100 is divided into two component sections 100a and 100b.

In accordance with the present technology, one or more electrical elements 200 may be electrically connected across gap 104. Similarly, one or more electrical elements 210 may be coupled between component section 100b of conductive line 100 and a portion of conductive line 102. Alternatively yet, an electrical element 212 may be coupled between component section 100a of conductive line 100 and a portion of conductive line 102. As presently illustrated, electrical elements 200, 210 and 212 may correspond to resistive elements each corresponding to a selected ohmic value.

In further embodiments of the present subject matter constructed in accordance with the present technology, electrical elements 200, 210, 212 may correspond to other component types including, but not limited to, resistors, capacitors, inductors, passive components, active components, and combinations thereof. Further, it is contemplated that each element 200, 210 need not be the same type or combination of element types. For example, it is contemplated that element 200 may correspond to a resistive element while element 210 and/or element 212 may correspond to a capacitive element. In some embodiments of the present technology, electrical elements 200, 210, 212 may correspond to printed passive components. It should be appreciated, however, that active components may also be used. It should be further appreciated by those of ordinary skill in the art that other elements and combination are possible so long as the chosen elements may be used to obtain the objectives desired.

With respect to such desired objectives, it is one objective of the present technology to provide a mechanism whereby the particular absorbent article 20 into which is incorporated technology in accordance with the present subject matter may be automatically recognized. In this light, in an exemplary embodiment, a resistive element 210 having a preselected ohmic value may be connected between conductive lines 100, 102. It should be appreciated that other element types or combinations of elements may also be employed. Generally the intent is to provide an element or combination of elements, the presence and electrical characteristics of which may be detected via a signaling device 110 coupled proximate to ends 232, 234, respectively, of conductive lines 100, 102 by way of a connecting mechanisms more fully describe in the previously mentioned incorporated application and generally indicated by dashed line box 230 and, in an alternate embodiment, to be described more fully later with reference to FIG. 3, dashed line box 230'.

In a first exemplary embodiment, electrical element 210 may be a resistor having a specific ohmic value. In addition electrical element 200 may also be a resistive element having another, possibly different, ohmic value. In some embodiments of the present subject matter the ohmic value of electrical element 200 may, in fact, be zero such that gap 104 may actually be electrically short circuited or may be omitted. Alternatively, in some embodiments of the present subject matter, plural gaps 104 may be provided along with optional plural electrical elements 200. In certain embodiments of the present subject matter, electrical elements 200, 210, and/or 212 may correspond to printed resistive components. Alternatively, electrical elements 200, 210, and/or 212 may take other known, available forms.

Depending on the value of the resistor 210, when signaling device 110 is attached to absorbent article 20, or, more specifically, to end portions 232, 234 of conductive lines 100, 102, a microcontroller associated with signaling device 110 would measure the resistance of resistor 210 and enable an audio theme to match the product. For example only, a male product might be indicated by a value of 100 kohms, while a female product may be indicated by a different resistive value. Verification of proper connection to the absorbent article 20 conductive lines 100, 102 may be indicated by playing of a gender appropriate sound. Detection of wetting of the absorbent article 20 may then be indicated by playing another gender appropriate sound.

In alternative embodiments, variations in resistive values of resistor 210 may signal a variety of gender specific products. For example, selected resistive values may be associated first with male specific products and then with other characteristics. Such other characteristics may include, but are not limited to, physical size and exact nature of the absorbent article 20 and, by extrapolation, the approximate weight of the potential wearer. By providing a signaling device 110 that is gender and/or product neutral, such device may be used in association with a wide variety of absorbent products ranging from those designed for infants to adults as well as also optionally taking into consideration gender of the potential wearer. Further, by providing a signaling device 110 with the capability of identifying the type of product that it has been connected to, the device can adjust internal firmware to compute different algorithms and/or selected different reference values accordingly to thereby provide user related and perceptible responses, signals and/or alarms. Product identifying resistor 210 or, alternatively other product identifying components or combinations, should be located in a non insult region of absorbent article 20 to prevent poor or inaccurate product detection.

In an exemplary arrangement, it should be appreciated that by providing a gender neutral signaling device 110 with the capability of detecting various characteristics of the article to which it may be associated, a number of possibilities exists. As a non-limiting example, the present technology may be used with an electronic hydration sensor that would allow the hydration sensor device to know what size and type of product it is placed on so that the electronic device could give a reading of percent hydration of the user. An electronic hydration device would be programmed to automatically differentiate among newborn, step one to step five diaper or size training pant and know the approximate weight of the wearer. Knowledge of product characteristics would also help the electronic hydration device to know the exact absorbent core in the product thereby increasing the accuracy of the unit. Such capability would allow a single electronic hydration device to operate with all sizes of absorbent articles up to adult sizes and make it much easier for a caregiver to read and use the hydration system. Commonly owned U.S. Patent Publication No. 20070083174, incorporated herein for all purposes, describes the use of an algorithm to determine multiple wettings based on different product sizes and absorbent structures so that wetness may be sensed regardless of the absorbent article being used.

Another possibility made available through the use of gender neutral signaling device 110 constructed in accordance with the present subject matter is to provide a device that is capable of determining proper operability between gender neutral signaling device 110 an the absorbent article to which it may be attached. As previously noted with respect to the exemplary embodiment of FIG. 2, proper connection of signaling device 110 to an absorbent article 20 may be signaled by way of one or more beep sounds or other appropriate visual and/or audible signals. In addition, in accordance with further embodiments of the present subject matter, signaling device 110 may determine whether it is coupled to a recognized absorbent article 20. Looked at from the perspective of the absorbent article 20, signaling device 110 can be inhibited from operation if it is not properly configured to operate with absorbent article 20. Such dual directional compatibility determination assists in assuring a wearer or user of a particular absorbent article and potentially associable signaling device 20 that such combination of absorbent article and signaling device will function properly.

With reference now to FIG. 3, an exemplary embodiment of the present subject matter providing for mutual absorbent article/signaling device operability verification will be described. As may be seen from a comparison with the embodiment illustrated in FIG. 2, many of the elements there illustrated are equivalent to those of FIG. 3 and carry similar identification notation. Further with respect to the embodiment illustrated in FIG. 3, it may be noticed that connector 230' is configured such that, in addition to connection points being provided for end portions 232, 234 of conductive lines 100, 102, an additional connection point 236 is provided so that an evaluation of any component such as electrical component 200 coupled across gap 104 or combinations of components such as electrical component 200 along with, for example, electrical component 210 may be made by signaling device 110.

Such evaluation provides a number of features and possibilities for the present subject matter. In a first instance, the signaling device 110 is able to determine whether the absorbent article 20 to which it may be coupled is appropriately configured to allow proper operation of the coupled signaling device 110. Further, the presence of a particular value electrical component 200 may function to inhibit operation of any unknown signaling device that may be coupled to absorbent article 20.

Further still, as previously noted it is contemplated that electrical components 200, 210, 212 may correspond to different component types although each are schematically illustrated for simplicity herein as resistive components. In one alternative exemplary configuration, one component may correspond to a resistive component while a second component may correspond to a capacitive component so as to form a charge/discharge RC circuit. Evaluation of the charge/discharge curves associated with such an RC circuit may be used to determine mutual compatibility between the absorbent article and the signaling device. Such mutual compatibility determination may be considered to operate as an electrical "lock and key" assuring that a recognized signaling device is coupled to a recognized absorbent article, and visa-a-versa.

Figure 4:
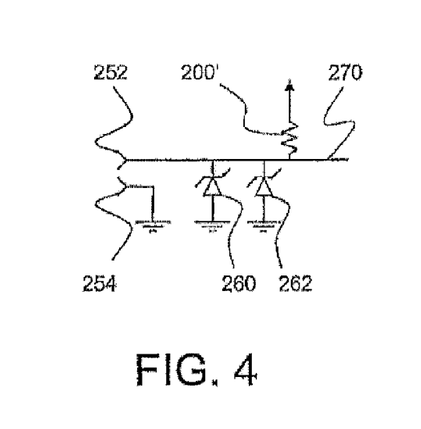
FIG. 4 is a partial schematic diagram of a signaling device as may be used with the absorbent article shown in FIG. 1.

With reference now to FIG. 4, a further embodiment of the present subject matter will be described. As illustrated in FIG. 4, there is shown a portion of the input circuitry of a signaling device as may be employed in for use with the present technology. Input terminals 252, 254 may be coupled by way of connectors 230 (FIG. 2) or 230' (FIG. 3) to selected connection points 232, 234, 236 associated with absorbent article 20's conductive lines 100, 102. In an exemplary arrangement, input terminal 254 may be connected to connection point 234 while input terminal 252 may be connected to connection point 232 or 236. Other connection configurations are possible, however.

With further reference to FIG. 4, it will be noticed that signal line 270 has coupled thereto a pair of diodes 260, 262 that serve to protect remaining portions of the signaling device's circuitry from electrical transients as may be inadvertently applied to input terminal 252. Further there is illustrated electrical component 200' coupled at one end to signal line 270 and at a second end to a power supply line within the signaling device. It should be appreciated by those of ordinary skill in the art that the second end of electrical component 200' may be coupled to other locations within the signaling device's circuitry.

A feature of the illustrated configuration is that electrical component 200' may correspond to one of components 200, 210, or 212 so that such components may actually be used as replacements for electrical component 200' within the input portion of the signaling device's circuitry. Such a modification may correspond to a means by which a "hardware key" is created for the device. Such a hardware key construction would further assure mutual compatibility and operation of an absorbent article and signaling device system in accordance with the present subject matter.

It should be appreciated by those of ordinary skill in the art that other configurations may be employed to provide such a hardware lock and key system in addition to use of the sensing elements. For example, inclusion of a number of gaps and/or short circuits associated with certain conductive components within the absorbent article may also be employed as a hardware lock and key system. In either case, however, attachment of the signaling device to an absorbent article can cause execution of a logic routine that, if the "key" is correct, allows the signaling device to operate correctly or, if the key is incorrect, disables the device. In the instance that a third party device was introduced to the absorbent article, such modifications would effect the measurement of the sensing element and create erroneous wetness readings or not allow the third party device to operate all together. On the other hand, in the instance that a third party absorbent article was introduced to the signaling device, lack of a correct key or any key at all within such third party absorbent article would prevent operation of the signaling device.

Figure 6:
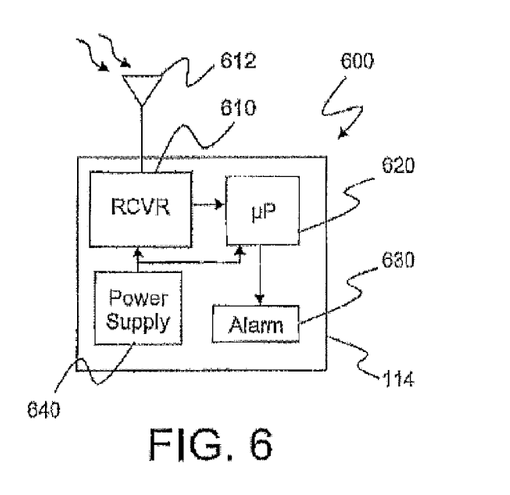
FIG. 6 is block diagram of a portion of an exemplary signaling device as may be used in combination with the absorbent article shown in FIG. 5.

With reference now to FIG. 6, there is illustrated a block diagram of a portion of an exemplary signaling device as may be used in combination with the absorbent article 20. As illustrated in FIG. 6, there is more specifically shown a receiver portion 114 of a signaling device 110 that may be used in combination with a transmitter portion 112 (FIG. 5) of signaling device 110 represented herein also by antenna element 238 (FIG. 3) associated with connector 230'. It should also be appreciated that such a transmitter and antenna may also be associated with connector 230 (FIG. 2) as more specifically also illustrated in FIG. 5 as transmitter device 112.

With further reference to FIG. 6, it may be seen that receiver portion 114 of signaling device 100 may, in an exemplary configuration, correspond to a receiver circuit 610 that may have as an input thereto an antenna 612. Antenna 612 may extend from a housing contain the remainder of the component parts of receiver 114 or may be fully contained therein. A microprocessor 620 or other similar device may receive one or more output signals from receiver 610 for processing in order to generate one or more perceptible signals or alarms from alarm component 630. As previously noted, alarms signal may take the form or visual, audible or vibrational signals or combinations thereof. Receiver 114 may draw operating power from power supply 640 which may correspond to a battery supply, or an externally energized supply. A suitable external supply may be taken from household supply lines, external battery sources such as automobile carried power sources or other external sources. Rechargeable batteries may also be employed and such may be charged from the previously mentioned external sources.

It should be kept in mind that, as previously mentioned above, signaling device 110 may correspond to a unitary device incorporating features of both transmitter 112 and receiver 114 into a single device designed to be coupled directly to absorbent article 20.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
    a chassis comprising an outer cover having an interior surface and an exterior surface and an absorbent structure positioned adjacent the interior surface of the outer cover;
    at least one conductive element contained in the chassis and forming part of a sensing circuit that is configured to sense the presence of a substance; and
    at least one electrically identifiable component associated with said at least one conductive element and located in a non insult region of the absorbent article, said at least one electrically identifiable component having an identifiable characteristic the presence of which permits the sensing circuit to recognize the absorbent article.

2. An absorbent article as defined in claim 1, wherein said at least one electrically identifiable component is coupled to said at least one conductive element.

3. An absorbent article as defined in claim 1, wherein said at least one electrically identifiable component comprises at least one gap proximate one end of said at least one conductive element, said at least one gap dividing said at least one conductive element into a first portion and a second portion.

4. An absorbent article as defined in claim 3, further comprising:
    at least one electrical component coupled across said gap.

5. An absorbent article as defined in claim 4, wherein said at least one electrical component is selected from the group consisting of resistors, capacitors, inductors, passive components, active components and combinations thereof.

6. An absorbent article as defined in claim 3, further comprising at least one second electrically identifiable component coupled to one of said first and second portions.

7. An absorbent article as defined in claim 6, further comprising:
    at least one second conductive element contained in the chassis and forming part of the sensing circuit, wherein said at least one second electrically identifiable component is coupled between said first portion of said at least one conductive element and said at least one second conductive element.

8. An absorbent article as defined in claim 6, further comprising:
    at least one second conductive element contained in the chassis and forming part of the sensing circuit, wherein said at least one second electrically identifiable component is coupled between said second portion of said first conductive element and said at least one second conductive element.

9. An absorbent article as defined in claim 7 or 8, wherein said at least one electrically identifiable component and said at least one second electrically identifiable component have different electrical characteristics.

10. An absorbent article as defined in claim 9, wherein said at least one electrically identifiable component comprises a resistive component and said at least one second electrically identifiable component comprises a capacitive component.

11. An absorbent article as defined in claim 1, wherein said at least one conductive element is configured to electrically connect to a signaling device, and wherein an identifiable characteristic of said at least one electrically identifiable component enables selected operability of said signaling device.

12. An absorbent article as defined in claim 11, wherein the selected operability of said signaling device comprises enabling or disabling operation of said signaling device.

13. An absorbent article as defined in claim 11, wherein the selected operability of said signaling device comprises adjusting operating parameters of said signaling device.

14. An absorbent article as defined in claim 13, wherein adjusting operating parameters of said signaling device comprises adjusting operating parameters based on gender specific characteristics of the absorbent article.

15. An absorbent article as defined in claim 13, wherein adjusting operating parameters of said signaling device comprises adjusting operating parameters based on size specific characteristics of the absorbent article.

16. An absorbent article as defined in claim 13, wherein adjusting operating parameters of said signaling device comprises adjusting operating parameters based on absorbent article type specific characteristics of the absorbent article.

17. An absorbent article as defined in claim 11, wherein the signaling device produces an audible, visible, and/or vibratory signal when activated.

18. An absorbent article as defined in claim 11, wherein the signaling device comprises a transmitter electrically connectable to the at least one conductive element, and a receiver, and wherein, the transmitter sends a wireless signal to the receiver which produces an audible, visible, and/or vibratory signal to a user when the signaling device is activated.

19. A method for providing absorbent article characteristic related signals, comprising:
   providing an absorbent article comprising an absorbent structure, at least one condition sensitive sensor, and at least one electrical component having electrically identifiable characteristics, said at least one electrical component being located in a non insult region of the absorbent article;
   providing a signaling device, the signaling device capable of producing selected user perceptible signal combinations;
   configuring the signaling device to be responsive to the at least one condition sensitive sensor and the at least one electrical component; and
   coupling the signaling device to the absorbent article,
   whereby the signaling device produces signal combinations responsive to a sensed condition and identifies the characteristics of the at least one electrical component and adjusts one or more of its operational conditions based thereon.

20. The method of claim 19, further comprising:
   providing at least one second electrical component having electrically identifiable characteristics;
   locating the at least one second electrical component in one of the absorbent article and signaling device; and
   disabling the signaling device upon failure to identify selected electrical characteristics of the at least one electrical component and the at least one second electrical component.

* * * * *